United States Patent [19]

Eriksson et al.

[11] 4,022,905
[45] May 10, 1977

[54] BENZYLIDENE HYDRAZINO-1,2,4-TRIAZOLES, PHARMACEUTICALS THEREWITH, AND METHOD OF USE

[75] Inventors: Hans Erik Eriksson, Holo; Gosta Lennart Florvall, Sodertalje, both of Sweden

[73] Assignee: Astra Lakemedel Aktiebolag, Sodertalje, Sweden

[22] Filed: Nov. 25, 1975

[21] Appl. No.: 635,140

[30] Foreign Application Priority Data

Dec. 11, 1974 Norway .............................. 4468/74

[52] U.S. Cl. ............................ 424/269; 260/240 G; 260/308 R
[51] Int. Cl.[2] ................ A61K 31/41; C07D 249/08
[58] Field of Search .................... 260/240 G, 308 R; 424/269

[56] References Cited

UNITED STATES PATENTS

| 3,516,995 | 6/1970 | Houlihan et al. | 260/240 G |
| 3,528,969 | 9/1970 | Houlihan et al. | 260/240 G |
| 3,769,278 | 10/1973 | Pifferi | 260/240 G |
| 3,850,915 | 11/1974 | Bruce | 260/240 G |
| 3,959,476 | 5/1976 | Eriksson et al. | 260/240 G X |

OTHER PUBLICATIONS

Kroger et al., "Synthesis & Reactions of 3-Hydrazino-4-amino 1,2,4-triazoles" in Annalen der Chemie, Bd. 664, 146–155 (1963).
Takimoto et al., "Synthesis & Reactions of 5-alkyl-4-amino-hydrazino-s-triazoles in S. Org. Chem., 30, No. 3, 711–713 (1965).

*Primary Examiner*—Allen B. Curtis
*Attorney, Agent, or Firm*—Brumbaugh, Graves, Donohue & Raymond

[57] ABSTRACT

Compounds having the general formula

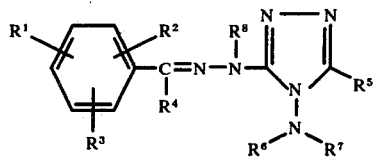

pharmaceutical preparations containing the compounds and use in the treatment of hypertension.

9 Claims, No Drawings

BENZYLIDENE HYDRAZINO-1,2,4-TRIAZOLES, PHARMACEUTICALS THEREWITH, AND METHOD OF USE

This invention relates to new triazoles and methods for their preparation. The invention also relates to the preparation of pharmaceutical preparations containing the triazoles and to methods for the pharmacological use of the triazoles.

PRIOR ART

Hypotensive agents have been known for a considerable time. It has also been known that these agents exert their effects through different mechanisms of action. Side-effects which have clinical implications of major importance are frequently encountered among these compounds. A well-known example is a rise in the blood pressure of shorter or longer duration after administration and before the onset of the desired fall in blood pressure. A further example is the sedative effect of these agents which may make these agents unsuitable for use by persons who perform any form of task which requires alertness, for instance car-driving.

OUTLINE OF INVENTION a. General Outline

We have found that certain compounds related to 4-amino-3-benzylidenehydrazino-1,2,4-triazoles have the ability of lowering the arterial blood pressure of unanesthetized animals with experimentally induced hypertension in oral doses which do not produce sedation or other apparent untoward effects.

More particular, these compounds have the general formula

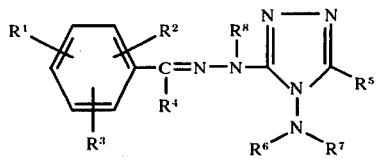

wherein $R^1$, $R^2$ and $R^3$ are the same or different and each represents a hydrogen atom, a lower alkyl group or a halogen atom, $R^4$ represents a hydrogen atom, a lower alkyl group or a pyridyl group, $R^5$, $R^6$, $R^7$ and $R^8$ are the same or different and each represents a hydrogen atom or a lower alkyl group, provided that $R^4$ is a lower alkyl group or a pyridyl group when $R^1$, $R^2$ and $R^3$ are hydrogen atoms and that $R^6$, $R^7$ and $R^8$ do not simultaneously represent a hydrogen atom.

The invention also comprises pharmaceutically acceptable salts of the compounds of the formula I.

Illustrative examples of radicals included in the above definitions are pyridyl group: 2-pyridyl
lower alkyl group: methyl, ethyl, n-propyl and iso-propyl
halogen atom: chlorine, bromine, iodine and fluorine.

By the expression "lower alkyl group" in this application is to be understood alkyl groups with 1, 2 or 3 carbon atoms.

The table below gives some compounds within the scope of this application

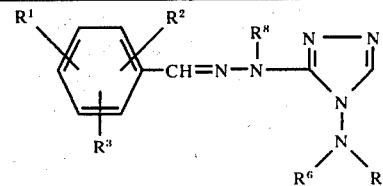

| $R^1$ | $R^2$ | $R^3$ | $R^6$ | $R^7$ | $R^8$ |
|------|------|------|------|------|------|
| 2-Cl | 6-Cl | H | $CH_3$ | H | H |
| 2-Cl | 6-Cl | H | $CH_3$ | $CH_3$ | H |
| 2-Cl | 6-Cl | H | $CH_3$ | $CH_3$ | $CH_3$ |
| 2-Cl | 6-Br | H | H | $CH_3$ | H |
| 2-Cl | 6-Br | H | $CH_3$ | $CH_3$ | H |
| 2-Cl | 6-Br | H | $CH_3$ | $CH_3$ | $CH_3$ |
| 2-Cl | 6-Cl | 4-$CH_3$ | $CH_3$ | H | H |
| 2-Cl | 6-Cl | 4-$CH_3$ | $CH_3$ | $CH_3$ | H |
| 2-Cl | 6-Cl | 4-$CH_3$ | $CH_3$ | $CH_3$ | $CH_3$ |
| 2-Cl | 6-$CH_3$ | 4-Cl | $CH_3$ | H | H |
| 2-Cl | 6-$CH_3$ | 4-Cl | $CH_3$ | $CH_3$ | H |
| 2-Cl | 6-$CH_3$ | 4-Cl | $CH_3$ | $CH_3$ | $CH_3$ | b. Pharmaceutical preparations

In clinical practice the compounds of the present invention will normally be administered orally, rectally or by injection, in the form of pharmaceutical preparations comprising the active ingredient either as a free base or as a pharmaceutically acceptable non-toxic, acid addition salt, e.g. the hydrochloride, hydrobromide, lactate, acetate, sulphate, sulphamate, and the like, in association with a pharmaceutically acceptable carrier. Accordingly, terms relating to the novel compounds of this invention whether generically or specifically are intended to include both the free amine base and the acid addition salts of the free base, unless the context in which such terms are used, e.g. in the specific examples would be inconsistent with the broad concept. The carrier may be a solid, semisolid or liquid diluent or capsule. These pharmaceutical preparations constitute a further aspect of this invention. Usually the active substance will constitute between 0.1 and 95% by weight of the preparation, more specifically between 0.5 and 20% by weight for preparations intended for injection and between 2 and 50% by weight for preparations suitable for oral administration.

To produce pharmaceutical preparations containing a compound of the invention in the form of dosage units for oral application, the selected compound may be mixed with a solid pulverulent carrier, e.g. lactose, saccharose, sorbitol, mannitol, starches such as potato starch, corn starch or amylopectin, cellulose derivatives, or gelatine, and a lubricant such as magnesium stearate, calciumstearate, polyethylene glycol waxes, and the like, and then compressed to form tablets. If coated tablets are required, the cores, prepared as described above, may be coated with a concentrated sugar solution which may contain e.g. gum arabic, gelatine, talcum, titanium dioxide, and the like. Alternatively, the tablet can be coated with a lacquer dissolved in a readily volatile organic solvent or mixture of organic solvents. Dyestuffs may be added to these coatings in order to readily distinguish between tablets containing different active substances or different amounts of the active compound.

For the preparation of soft gelatine capsules (pearl-shaped closed capsules) consisting of gelatine, and for example, glycerol or similar closed capsules, the active substance may be admixed with a vegetable oil. Hard gelatine capsules may contain granulates of the active substance in combination with solid, pulverulent carriers such as lactose, saccharose, sorbitol, mannitol, starches (e.g. potato starch, corn starch or amylopectin), cellulose derivatives or gelatine.

Dosage units for rectal aplication can be prepared in the form of suppositories comprising the active substance in admixture with a neutral fatty base, or gelatine rectal capsules comprising the active substance in admixture with vegetable oil or paraffin oil.

Liquid preparations for oral aplication may be in the form of syrups or suspensions, for example, solutions containing from about 0.2% to about 20% by weight of the active substance herein described, the balance being sugar and a mixture of ethanol, water, glycerol, and propyleneglycol. Optionally such liquid preparations may contain coloring agents, flavoring agents, saccharine and carboxymethylcellulose as a thickening agent.

Solutions for parenteral applications by injection can be prepared in an aqueous solution of a water-soluble pharmaceutically acceptable salt of the active substance preferably in a concentration of from about 0.5% to about 10% by weight. These solutions may also contain stabilizing agents and/or buffering agents and may conveniently be provided in various dosage unit ampoules.

c. Preferred embodiment

The preferred compounds of the invention have the structural formula

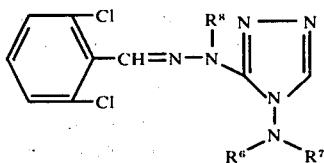

wherein $R^6$ is a hydrogen atom or a methyl group, $R^7$ is a hydrogen atom or a methyl group and $R^8$ is a hydrogen atom or a methyl group.

The compound of the formula

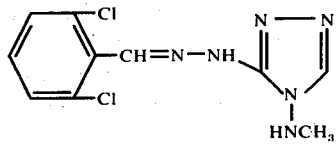

is particularly interesting.

Preferably these compounds will be prepared and used in the form of their hydrochloride salts.

d. Methods of preparation

A. Generally the compounds of the formula I are prepared via the following route ($R^1$, $R^2$, $R^3$, $R^4$, $R^5$, $R^6$, $R^7$ and $R^8$ have the above given definitions):

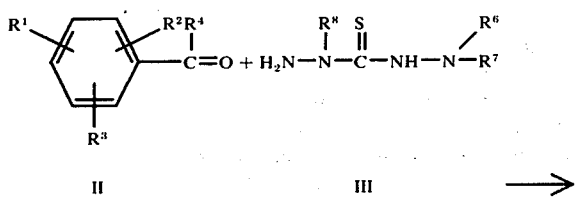

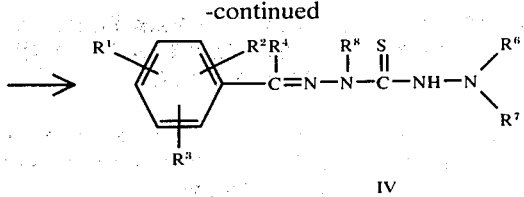

Substituted monothiocarbohydrazones of the formula IV are prepared by treating of aldehydes or ketones of the formula II with a thiocarbohydrazide of the formula III. The reaction is preferably performed at elevated temperatures in a suitable solvent e.g. ethanol or acetic acid.

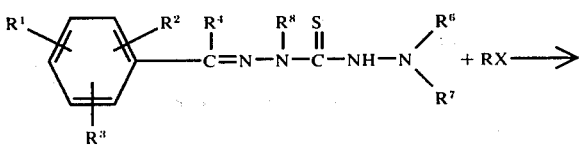

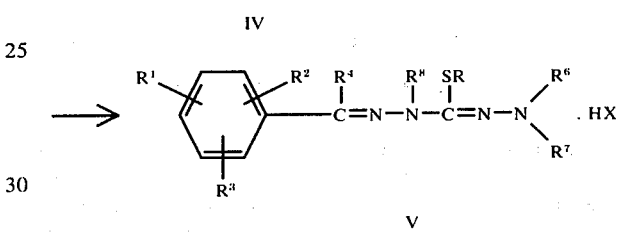

(R = alkyl or aryl; X = halogen)

The substituted monothiocarbohydrazones IV are transformed into S-alkylisothiocarbohydrazones V by means of an halide or a dialkylsulphate such as methyl iodide, ethyl iodide, dimethyl sulphate, benzyl chloride and the like.

The reaction may be conducted in solvents such as ethanol from about room temperature to reflux temperature. The addition salt of V may be converted to the free base using conventional techniques, such as treating the salt with sodium carbonate solution.

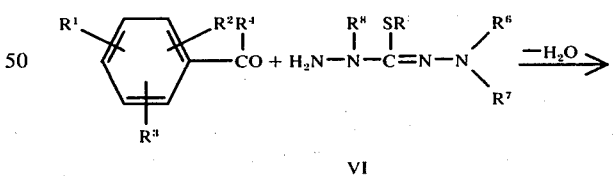

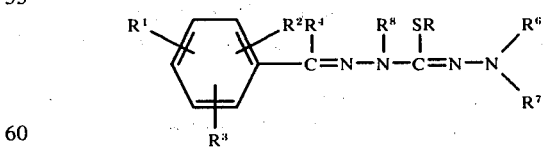

Alternatively, the S-alkylisothiocarbohydrazones can also be prepared from the corresponding aldehydes or ketones and a properly substituted S-alkylisothiocarbohydrazide VI. The reaction is performed as for the monothiocarbohydrazones.

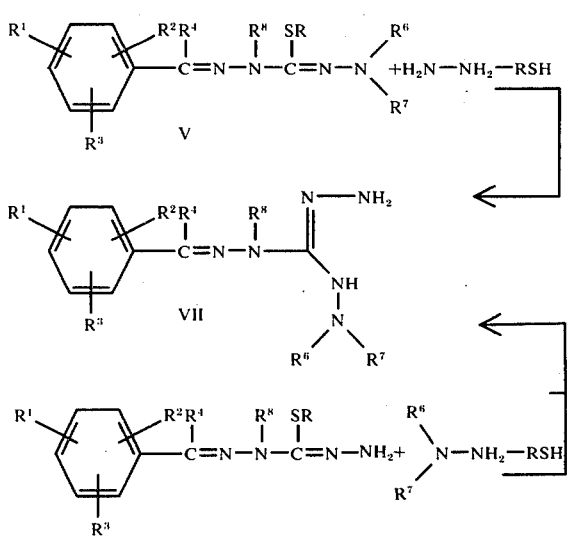

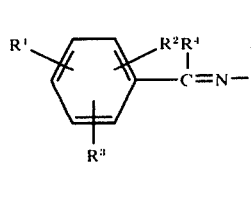

The addition salts or the free bases of the S-alkylisothiocarbohydrazones V are reacted with hydrazine or N,N-dialkylhydrazines yielding substituted 1-benzylideneamino-2,3-diaminoguanidines VII. The reaction may be conducted in solvents such as alcohols or in aqueous mixtures thereof. The products may be recovered using conventional techniques, such as filtration. The acid addition salts may be obtained from the free base by salifying.

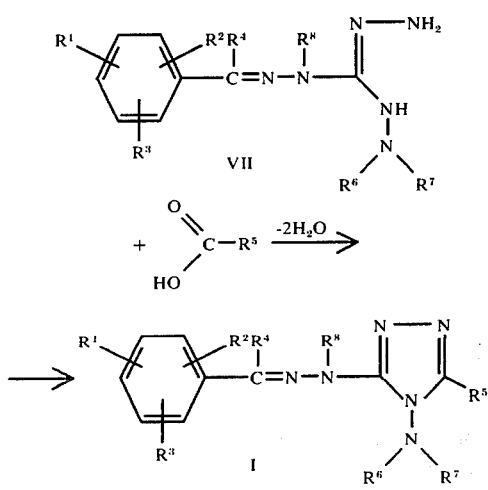

Compounds of the formula I are prepared from the substituted 1-benzylideneamino-2,3-diaminoguanidines VII by reaction with carboxylic acids at elevated temperatures. The obtained 4-amino-3-benzylidenehydrazino-1,2,4-triazoles of formula I are preferably isolated as the addition salts, e.g. the hydrochlorides.

The intermediate compounds of formula III and VI are known or may be prepared according to methods disclosed in the literature.

B. Compounds of the formula I wherein $R^7$ and $R^8$ represent a hydrogen atom and $R^6$ is an alkyl group can be prepared via the following route ($R^1$, $R^2$, $R^3$, $R^4$ and $R^5$ have the previously given definitions):

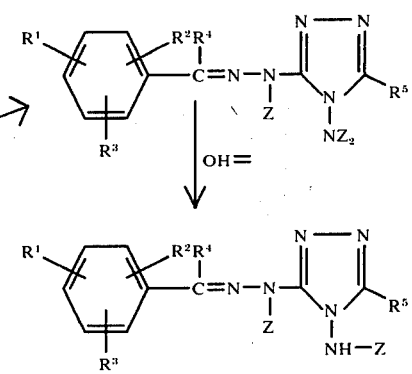

(Z= a N-protecting group, such as an arylsulphonyl group, an alkylsulphonyl group, an acyl group or an alkoxycarbonyl group).

The amides in the scheme above are prepared from the corresponding amines. The reaction involves the acylation of the amine or amine salt with e.g. chloroformic esters, sulphonyl halides, acyl halides or acid anhydrides.

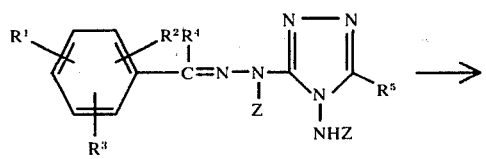

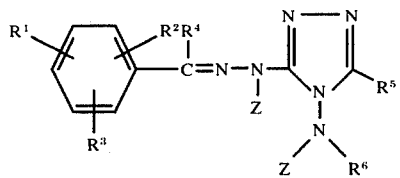

The amides is treated with an alkyl halide or a dialkyl sulphate. The reaction is preferably performed in a suitable solvent such as ethanol or water and in the presence of a base such as sodium hydrogen carbonate or sodium hydroxide.

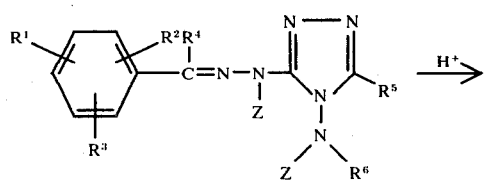

-continued

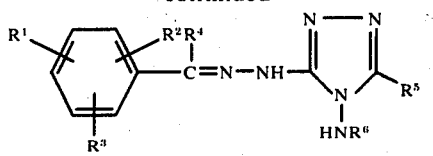

In the last step hydrolysis affords the desired compounds.

a. Working examples

This invention is further illustrated by the following examples.

EXAMPLE 1

4-Acetamido-3-[1-acetyl-2-(2,6-dichlorobenzylidene)-hydrazino]-1,2,4-triazole

Alternative A

To a warm solution (~ 45 °C) of 46.0 g of 4-amino-3-(2,6-dichlorobenzylidenehydrazino)-1,2,4-triazole hydrochloride in 150 ml of dry pyridine is added dropwise while stirring 25 ml of acetyl chloride. The mixture is stirred overnight at room temperature and is then poured into 1 liter of ice water. The precipitate formed is collected by filtration and washed with water. Yield: 43.5 g, m.p. 205°–210°.

The crude product is recrystallized from dilute dioxane yielding 31.6 g of the compound, melting at 211°–212°. Calculated for $C_{13}H_{12}Cl_2N_6O_2$: C 43.96, H 3.41, Cl 19.95, N 23.66, O 9.01. Found: C 44.0, H 3.43, Cl 20.1, N 23.8, O8.95.

Alternative B

To a stirred suspension of 15 g of 4-diacetylamino-3-[1-acetyl-2-(2,6-dichlorobenzylidene) hydrazino]-1,2,4-triazole in a mixture of 100 ml of ethanol and 200 ml of water is added 50 ml of saturated sodium carbonate solution. The stirred mixture is heated in a boiling water bath for 10 minutes. The obtained solution is diluted with water to a volume of 1 liter and is then acidified with acetic acid. The precipitate is filtered off and washed with water. Yield: 8.1 g, m.p. 209°–211°. The crude compound is recrystallized from dilute dioxane yielding 6.0 g of the compound, melting at 211°–212°.

4-Diacetylamino-3-[1-acetyl-2-(2,6-dichlorobenzylidene) hydrazino]-1,2,4-triazole A solution of 30.8 g of 4-amino-3-(2,6-dichlorobenzylidene- hydrazino)-1,2,4-triazole hydrochloride in 100 ml of acetic anhydride is heated at reflux temperature for 1.5 hours. After cooling 600 ml of water is added. The mixture is then stirred at room temperature for 2 hours. The obtained precipitate is collected and washed with water. Yield: 35.6 g, m.p. 140°–150°. The product is recrystallized from diluted ethanol. Yield: 15.1 g, m.p. 178°–179°.

Calculated for $C_{15}H_{14}Cl_2N_6O_3$; C 45.36, H 3.55, Cl 17.85, N 21.16, O 12.08

Found: C 44.9, H 4.08, Cl 17.8, N 20.9, O 12.1.

4-(N-Methylacetamido)-3-[-1-acetyl-2-(2,6-dichlorobenzylidene)-hydrazino]-1,2,4-triazole To a solution of 31.5 g of 4-acetamido-3[1-acetyl-2-(2,6-dichlorobenzylidene) hydrazino]-1,2,4-triazole and 53.0 g of sodium carbonate in 400 ml of water is added dropwise, while stirring and cooling in an ice bath, 40 ml of dimethyl sulphate (2 h). After the addition the mixture was stirred for 2,5 h while cooling in ice and left overnight at room temperature. The obtained precipitate is collected and recrystallized twice from dioxane-isopropyl ether. Yield: 7.3 g, m.p. 167°–169°.

Calculated for $C_{14}H_{14}Cl_2N_6O_2$; C 45.54, H 3.82, Cl 19.20, N 22.76, O 8.67.

Found: C 45.8, H 4.07, Cl 19.2, N 22.7, O 9.01.

3-(2,6 Dichlorobenzylidenehydrazino)-4-ethylamino-1,2,4-triazole-hydrochloride

A solution of 6.2 g of 4-(N-methylacetamido-3-[1-acetyl-2-(2,6-dichlorobenzylidene) hydrazino]-1,2,4-triazole in 50 ml of acetic acid, 50 ml of concentrated hydrochloric acid and 50 ml of water is heated at reflux overnight. The solution is evaporated and the residue is recrystallized from ethanol-isopropyl ether. Yield 2.4 g, m.p. 205°–207°. Two more recrystallizations from the same solvent mixture gave 1.5 g of an analytically pure sample, m.p. 210°–211°.

Calculated for $C_{10}H_{10}Cl_2N_6$ HCl: C 37.34, H 3.45, Cl 33.07, N 26.13.

Found: C 37.5, H 3.56, Cl 33.3, N 25.7.

EXAMPLE 2

1-[2,6-dichlorobenzylidene]-5,5-dimethyl-thiocarbohydrazine 5.4 g of 1,1-dimethylthiocarbohydrazine and 7.1 g of 2,6-dichlorobenzaldehyde was refluxed in 100 ml of dry ethanol for 18 hours. The reaction mixture was cooled, and the solid precipitate was filtered off. Yield 7.3 g. m.p. 205 °C.

1-[2,6-dichlorobenzylidene]-5,5,5-trimethylisothiocarbohydrazine 7.3 of 1-[2,6-dichlorobenzylidene ]-5,5-dimethyl-thiocarbohydrazine and 3.5 g of $CH_3I$ in 50 ml of dry ethanol is refluxed for 2 hours. The reaction mixture is evaporated, ether is added and the crystalline residue filtered. Yield 5.2 g of a low melting solid (<50 °C).

1-[2,6-dichlorobenzylidene]-2-dimethylamino-3-aminoguanidine 0.6 g of hydrazinehydrate and 5 g of 1 [2,6-dichlorobenzylidene]-5,5,5-trimethylisothiocarbohydrazine were dissolved in 50 ml of dry ethanol and stirred for 18 hours. The solvent is evaporated and water added. pH is adjusted to 8–10 and the precipitate is filtered. It is then dissolved in HCl-acid, the excess of which is evaporated. Yield 2.6 g. m.p. 183° C.

3-[2,6-dichlorobenzylidenehydrazino]-4-dimethylamino-1,2,4-triazole 2.5 g of 1-[2,6-dichlorobenzylidene]-2-dimethylamino-3-aminoguanidine is dissolved in 25 ml of 85% formic acid for one hour. The mixture is evaporated and the residue dissolved in 25 ml 6 N HCl-acid and refluxed for another 30 min. The reaction mixture is evaporated and the residue recrystallized. Yield 1 g. m.p. 189° C.

f. Biological test

The antihypertensive effects of the hydrochloride salt of the compound of the invention with the designation FLA 486 having the formula

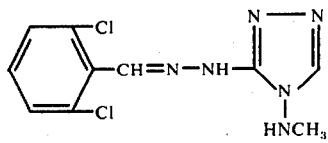

have been compared with those of FLA 136 with the formula

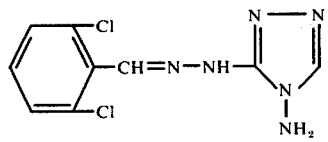

in spontaneously hypertensive rats of the SHR/N strain (Mollegaard Hansens Avlslaboratorier A/S, Denmark). The animals were prepared for measurements of the arterial blood pressure through a catheter implanted into the abdominal aorta and exteriorized at the base of the neck. Groups of two rats were given three consecutive daily oral doses of the test compounds. Measurements were performed before and three hours after administration to the unanesthetized animal. The effective antihypertensive dose of FLA 486, defined as the dose which reduced the mean arterial blood pressure more than 30 mm Hg was 5–10 mg/kg. The corresponding value for FLA 136 was 5–10 mg/kg.

We claim:

1. A compound of the formula

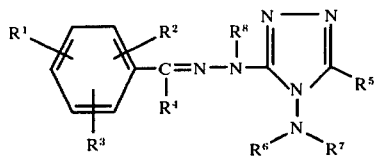

or a pharmaceutically acceptable salt thereof wherein $R^1$, $R^2$ and $R^3$ are the same or different and each represents a hydrogen atom, a lower alkyl group or a halogen atom, $R^4$ represents a hydrogen atom, a lower alkyl group, $R^5$, $R^6$, $R^7$ and $R^8$ are the same or different and each represents a hydrogen atom or a lower alkyl group, provided that $R^4$ is a lower alkyl group when $R^1$, $R^2$ and $R^3$ are hydrogen atoms and that $R^6$, $R^7$ and $R^8$ do not simultaneously represent a hydrogen atom.

2. A compound according to claim 1 characterized by the formula

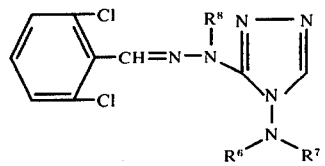

or a pharmaceutically acceptable salt thereof wherein $R^6$ is a hydrogen atom or a methyl group, $R^7$ is a hydrogen atom or a methyl group and $R^8$ is a hydrogen atom or a methyl group.

3. A compound according to claim 2 characterized by the formula

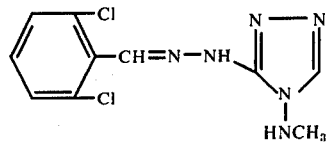

or a pharmaceutically acceptable salt thereof.

4. A pharmaceutical preparation which comprises as active ingredient a therapeutically effective amount of at least one compound of the formula

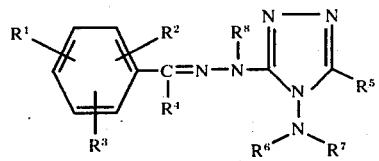

or a pharmaceutically acceptable salt thereof wherein $R^1$, $R^2$ and $R^3$ are the same or different and each represents a hydrogen atom, lower alky group or a halogen atom; $R^4$ represents a hydrogen atom, a lower alkyl group, $R^5$, $R^6$, $R^7$ and $R^8$ are the same or different and each represents a hydrogen atom or a lower alkyl group, provided that $R^4$ is a lower alkyl group when $R^1$, $R^2$ and $R^3$ are hydrogen atoms and that $R^6$, $R^7$ and $R^8$ do not simultaneously represent a hydrogen atom, in association with a pharmaceutically acceptable carrier.

5. A pharmaceutical preparation according to claim 4 which comprises as active ingredient a thereapeutically effective amount of at least one compound of the formula

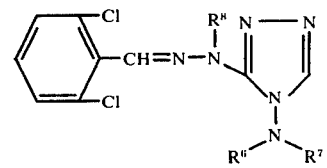

or a pharmaceutically acceptable salt thereof wherein $R^6$ is a hydrogen atom or a methyl group, $R^7$ is a hydrogen atom or a methyl group and $R^8$ is a hydrogen atom or a methyl group, in association with a pharmaceutically acceptable carrier.

6. A pharmaceutical preparation according to claim 5 which comprises as active ingredient a therapeutically effective amount of a compound of the formula

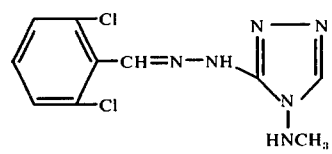

or a pharmaceutically acceptable salt thereof in association with a pharmaceutically acceptable carrier.

7. A method for the treatment of hypertension, characterized in administration to a host suffering from such ailment a therapeutically acceptable amount of a compound of the formula

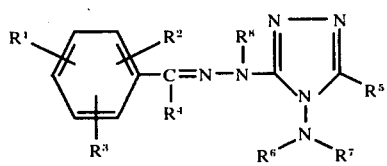

or a pharmaceutically acceptable salt thereof wherein $R^1$, $R^2$ and $R^3$ are the same or different and each represents a hydrogen atom, a lower alkyl group or a halogen atom, $R^4$ represents a hydrogen atom, a lower alkyl group, $R^5$, $R^6$, $R^7$ and $R^8$ are the same or different and each represents a hydrogen atom or a lower alkyl group, provided that $R^4$ is a lower alkyl group when $R^1$, $R^2$ and $R^3$ are hydrogen atoms and that $R^6$, $R^7$ and $R^8$ do not simultaneously represent a hydrogen atom.

8. A method according to claim 7 characterized in the administration of a compound of the formula

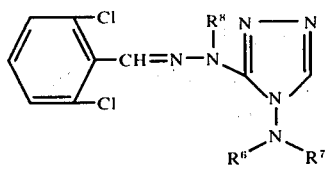

or a pharmaceutically acceptable salt thereof wherein $R^6$ is a hydrogen atom or a methyl group, $R^7$ is a hydrogen atom or a methyl group and $R^8$ is a hydrogen atom or a methyl group.

9. A method according to claim 8, characterized in the administration of a compound of the formula

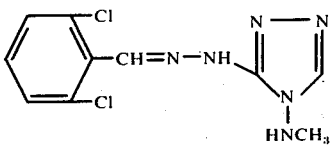

or a pharmaceutically acceptable salt thereof.

* * * * *

Disclaimer 4,022,905.—*Hans Erik Eriksson*, Holo, and *Gosta Lennart Florvall*, Sodertalje, Sweden. BENZYLIDENE HYDRAZINO - 1,2,4 - TRIAZOLES, PHARMACEUTICALS THEREWITH, AND METHOD OF USE. Patent dated May 10, 1977. Disclaimer filed Feb. 18, 1977, by the assignee, *Astra Lakemedel Aktiebolag*.

The term of this patent subsequent to May 25, 1993 has been disclaimed.
[*Official Gazette August 16, 1977.*]